(12) United States Patent
Mellata (10) Patent No.: US 9,198,950 B2
(45) Date of Patent: Dec. 1, 2015

(54) RECOMBINANT BACTERIUM COMPRISING A TOXIN/ANTITOXIN SYSTEM

(75) Inventor: Melha Mellata, Scottsdale, AZ (US)

(73) Assignee: Arizona Board of Regents on behalf of Arizona State University, Tempe, AZ (US)

( * ) Notice: Subject to any disclaimer, the term of this patent is extended or adjusted under 35 U.S.C. 154(b) by 106 days.

(21) Appl. No.: 13/989,692

(22) PCT Filed: Nov. 22, 2011

(86) PCT No.: PCT/US2011/061896
§ 371 (c)(1),
(2), (4) Date: Sep. 5, 2013

(87) PCT Pub. No.: WO2012/087483
PCT Pub. Date: Jun. 28, 2012

(65) Prior Publication Data
US 2013/0337013 A1    Dec. 19, 2013

Related U.S. Application Data

(60) Provisional application No. 61/417,046, filed on Nov. 24, 2010, provisional application No. 61/417,030, filed on Nov. 24, 2010.

(51) Int. Cl.
*A61K 39/112* (2006.01)
*A61K 39/02* (2006.01)
*A61K 49/00* (2006.01)
*A61K 38/16* (2006.01)
*C12N 1/38* (2006.01)
*C12N 15/74* (2006.01)
*A61K 39/00* (2006.01)

(52) U.S. Cl.
CPC .......... *A61K 38/164* (2013.01); *A61K 39/0275* (2013.01); *C12N 1/38* (2013.01); *C12N 15/74* (2013.01); *A61K 2039/522* (2013.01); *A61K 2039/523* (2013.01); *A61K 2039/585* (2013.01)

(58) Field of Classification Search
CPC ... A61K 39/00; A61K 39/02; A61K 39/0275; A61K 48/00; A61K 49/00
USPC .................. 424/9.1, 9.2, 184.1, 200.1, 234.1, 424/236.1, 258.1
See application file for complete search history.

(56) References Cited

U.S. PATENT DOCUMENTS

| 6,610,529 | B1 | 8/2003 | Curtiss, III et al. |
| 6,969,513 | B2 | 11/2005 | Galen |
| 2006/0275255 | A1 | 12/2006 | Gudkov |
| 2008/0248066 | A1 | 10/2008 | Dubensky et al. |

FOREIGN PATENT DOCUMENTS

WO    2012087483    6/2012

OTHER PUBLICATIONS

PCT/US2011/061896 (WO 2012/087483)—International Search Report and Written Opinion of the International Searching Authority, Apr. 5, 2012.

*Primary Examiner* — Rodney P Swartz
(74) *Attorney, Agent, or Firm* — Rebecca C. Riley-Vargas; Polsinelli PC (57) ABSTRACT

The present invention encompasses recombinant bacteria suitable for live attenuated vaccines, and methods of use thereof. One aspect of the present invention encompasses a recombinant *Salmonella* bacterium. The bacterium comprises a first promoter operably linked to a nucleic acid encoding a toxin and a second promoter operably linked to a nucleic acid encoding an antitoxin, wherein the second promoter is inactive in vivo, but active in vitro.

15 Claims, 2 Drawing Sheets

SEQUENCE LISTING

```
<160> NUMBER OF SEQ ID NOS: 1

<210> SEQ ID NO 1
<211> LENGTH: 36
<212> TYPE: DNA
<213> ORGANISM: Erwinia carotovora

<400> SEQUENCE: 1
aggtgatttg ctacctttaa gtgcagctag aaattc                              36
```

RECOMBINANT BACTERIUM COMPRISING A TOXIN/ANTITOXIN SYSTEM

GOVERNMENTAL RIGHTS

This invention was made with government support under 1R21AI090416-01 awarded by the National Institutes of Health. The government has certain rights in the invention.

FIELD OF THE INVENTION

The present invention encompasses recombinant bacteria suitable for live attenuated vaccines, and methods of use thereof. The present invention further encompasses recombinant bacteria and methods for inhibiting tumors.

BACKGROUND OF THE INVENTION

Live attenuated vaccines are considered among the most powerful tools for disease control and potentially disease eradication. Although vaccines have made a major contribution to public health, there are still significant deaths from diseases for which vaccines are not available. When vaccines are available, they may not be completely satisfactory in terms of safety, efficacy, and costs.

Attenuated bacteria that are unable to cause clinical diseases, but do trigger a self-limiting infection leading to the stimulation of protective immunity, represent an attractive method to prevent and/or treat infections. Because of their capacity for efficient mucosal antigen delivery, live attenuated *Salmonella enterica* serovar *Typhimurim* (*S. Typhimurium*) strains are considered good candidates for vaccine vectors. They have been used for expression of foreign antigens to induce mucosal, humoral, and cellular immune responses against both the attenuated carrier *Salmonella* and the expressed foreign protective antigen. *S. Typhimurium* gains access to internal lymphoid tissues by attaching to and invading through gut associated lymphoid tissues (GALT, including Peyer's patches) and stimulating a generalized secretory immune response. The ability of most attenuated vaccines to replicate in the host, results in the elicitation of strong and long-lasting immune responses, which mimic those stimulated by natural infections. A variety of attenuating mutations and antibiotic-free balanced-lethal plasmid stabilization systems has been developed for this purpose.

It is however essential to develop better, safer, and cheaper vaccines capable of promoting long-lasting protection.

Cancer is one of the leading killers in the US and around the world. The World Health organization (WHO) estimates that more than 20 million individuals are living with cancer and 84 million people will die of cancer between 2005 and 2015. The percentage of cancer-related deaths attributable just to diet and tobacco is as high as 60-70% worldwide. Moreover, more than 10 million people worldwide are expected to be diagnosed with cancer this year. In the US, almost 1.5 million people are diagnosed with cancer annually. It is the second leading cause of death after heart attacks and accounts for about 23% of total deaths. The five cancers that are associated with the highest number of deaths in the US are lung, breast, colorectal, prostate, and pancreatic. Cancer is also a major cause of morbidity and lost productivity costing billions of dollars to the US health care system. The cost due to both morbidity and premature mortality from cancer was estimated at $139.9 billion.

Cancer is a complex, multifactorial process. The disease is caused by both internal factors, such as genetics, hormones, and immune conditions and environmental/acquired factors, including environment, lifestyle and infections. Carcinogens and other risk factors affect chronic inflammation leading to tumorigenic pathway activation. Tumor cells are characterized by their low antigenicity and their high tumorigenicity, conditions that enable cancer cells to escape the immune system, allowing them to proliferate aggressively and metastasize to other tissues. Cancer patients often exhibit immunosuppression that primarily involves regulatory T cells and myeloid-derived suppressor cells.

Multiple approaches are used to treat different cancers including surgery, chemotherapy, biotherapy, radiotherapy, or a combination of these. Despite significant contributions to cancer treatment, the disease still causes high death rates. The limitations of these therapies are related to their toxicity, their ineffectiveness in targeting tumors, and their poor accessibility to tumor tissue. The fact that most tumors are characterized by their poorly vascularized hypoxic areas that limit the efficacy of radiation and chemotherapeutic drugs just magnifies the challenges in treatment. Hence, there is a need in the art for improved cancer treatments.

SUMMARY OF THE INVENTION

One aspect of the present invention encompasses a recombinant *Salmonella* bacterium. The bacterium comprises a first promoter operably linked to a nucleic acid encoding a toxin and a second promoter operably linked to a nucleic acid encoding an antitoxin, wherein the second promoter is inactive in vivo, but active in vitro.

Another aspect of the present invention encompasses a method for inducing an immune response in a subject. The method comprises administering to the subject a recombinant *Salmonella* bacterium, the bacterium comprising a first promoter operably linked to a nucleic acid encoding a toxin and a second promoter operably linked to a nucleic acid encoding an antitoxin, wherein the second promoter is inactive in vivo, but active in vitro.

Yet another aspect of the present invention encompasses a vaccine. The vaccine comprises a recombinant *Salmonella* bacterium. The bacterium comprises a first promoter operably linked to a nucleic acid encoding a toxin and a second promoter operably linked to a nucleic acid encoding an antitoxin, wherein the second promoter is inactive in vivo, but active in vitro.

Other aspects and iterations are described more thoroughly below.

DETAILED DESCRIPTION

The present invention encompasses a recombinant bacterium. Advantageously, in one aspect, a bacterium of the invention is capable of expressing an antitoxin in vitro, but not in vivo, resulting in death of the bacterium via the action of a toxin. Such action may be used as a biocontainment mechanism, and may also serve to release an antigen in a cell of a host. As a result, a bacterium of the invention may be used as a live attenuated vaccine vector that will result in death of the bacterium in vivo, after effective delivery of one or more antigens of interest. The present invention further encompasses methods of using a recombinant bacterium of the invention as a vaccine.

In another aspect, a recombinant bacterium of the invention is capable of expressing a nucleic acid encoding a toxin in a tumor cell. Advantageously, a bacterium of the invention is further capable of expressing a nucleic acid encoding an antitoxin in a non-tumor cell. As a result, a bacterium of the invention may be used in vivo to deliver a toxin to a tumor cell without substantial damage to non-tumor cells.

As used herein, "tumor cell" refers to a malignant cell. Suitable tumor cells may include a carcinoma cell, a sarcoma cell, a myeloma cell, a leukemia cell, or a lymphoma cell. Similarly, a "non-tumor cell" refers to a cell that is benign. A tumor cell is typically mammalian, and may, in certain embodiments, be derived from a rodent, a non-human primate, or a human.

I. Bacterium of the Invention

A *Salmonella* bacterium of the invention may be derived from several different *Salmonella* strains. Some embodiments of the instant invention comprise a species or subspecies of the *Salmonella* genera. For instance, the recombinant bacterium may be a *Salmonella enterica* serovar. In an exemplary embodiment, a bacterium of the invention may be derived from *S. enterica* serovar *Typhimurium*, hereafter referred to as *S. Typhimurium*, and also from *S. Typhi, S. Paratyphi, S. Enteritidis, S. Choleraesius, S. Arizona*, or *S. Dublin*. In an exemplary embodiment, the recombinant bacterium is derived from *S. Typhimurium*.

A recombinant *Salmonella* bacterium of the invention comprises, in part, a first promoter operably linked to a nucleic acid encoding a toxin and a second promoter operably linked to a nucleic acid encoding an antitoxin. Each is discussed in more detail below.

(a) First Promoter Operably Linked to a Nucleic Acid Encoding a Toxin

A *Salmonella* bacterium of the invention comprises, in part, a first promoter operably linked to a nucleic acid encoding a toxin. The term "promoter", as used herein, may mean a synthetic or naturally-derived molecule that is capable of conferring, activating or enhancing expression of a nucleic acid. A promoter may comprise one or more specific transcriptional regulatory sequences to further enhance expression and/or to alter the spatial expression and/or temporal expression of a nucleic acid. The term "operably linked," as used herein, means that expression of a nucleic acid is under the control of a promoter with which it is spatially connected. A promoter may be positioned 5' (upstream) of the nucleic acid under its control. The distance between the promoter and a nucleic acid to be expressed may be approximately the same as the distance between that promoter and the native nucleic acid sequence it controls. As is known in the art, variation in this distance may be accommodated without loss of promoter function.

A suitable first promoter is generally active in vivo (i.e. in a host), and may also be active in vitro. As used herein, "active" refers to the minimum level of transcription of a nucleic acid sequence encoding a toxin to induce the death of the bacterium. Methods for determining the minimum level of transcription of a nucleic acid sequence encoding a toxin needed to induce death of a bacterial cell are known in the art. For instance, see the Examples. In one embodiment, a first promoter is the native promoter of the toxin.

In another embodiment, a suitable first promoter is active in a tumor cell, but substantially inactive in a non-tumor cell. As used herein, "active in a tumor cell" refers to the minimum level of transcription of a nucleic acid sequence encoding a toxin to cause the death of a tumor cell or to decrease the growth and/or proliferation of a tumor cell. As used herein, "substantially inactive in a non-tumor cell" refers to less than 20% of the "active" level of the promoter. In some embodiments, "substantially inactive" refers to less than 15%, 14%, 13%, 12%, 11%, 10%, 9%, 8%, 7%, 6%, 5%, 4%, 3%, 2%, or 1% of the active level of the promoter. Methods for determining the minimum level of transcription of a nucleic acid sequence encoding a toxin to cause the death of a tumor cell or to decrease the growth and/or proliferation of a tumor cell are known in the art. For instance, see the Examples.

In some embodiments where a first promoter is active in a tumor cell, but substantially inactive in a non-tumor cell, the first promoter is active under hypoxic conditions. For instance, a first promoter may be Pr2 promoter. Non-limiting examples may include the pfIE or ansB promoters. In another embodiment, a first promoter may be active in a telomerase-positive tumor cell. By way of non-limiting example, a first promoter may be a human telomerase reverse transcriptase promoter. A promoter of the invention may be derived from a prokaryotic cell or a eukaryotic cell. In all instances, though, a first promoter must be active in a tumor cell and substantially inactive in a non-tumor cell.

As used herein, "toxin" refers to an amino acid polymer encoded by a nucleic acid sequence, so that, when the nucleic acid sequence is transcribed into an RNA molecule, or translated into an amino acid sequence, it is harmful to a cell. In one embodiment, a toxin may induce apoptosis of a cell. In another embodiment, a toxin may induce pyroptosis of a cell. In still another embodiment, a toxin may induce necrosis of a cell. In yet another embodiment, a toxin may induce cell lysis. In exemplary embodiments, a toxin of the invention is part of a prokaryotic toxin/antitoxin system. Generally speaking there are three types of prokaryotic toxin/antitoxin systems. Type I toxins are typically small, hydrophobic proteins which confer their toxicity by damaging cell membranes. Non-limiting examples of a Type I toxin may be found in Table A.

In a Type II system, a labile protein antitoxin tightly binds and inhibits the activity of a stable toxin. Non-limiting examples of a Type II toxin may also be found in Table A.

Type III toxin-antitoxin systems rely on direct interaction between a toxic protein and an RNA antitoxin. The toxic effects of the protein are neutralized by the RNA sequence. A non-limiting example of a Type III toxin is ToxN, which is neutralized by 5.5 direct repeats of a 36 nucleotide motif (AGGTGATTTGCTACCTTTAAGTGCAG CTAGAAATTC, SEQ ID NO:1).

Toxins may also be homologs or derivatives of the toxins detailed above. Generally speaking a homolog or derivative will have greater than 80% sequence identity to a known toxin, and will be harmful to a cell. Methods of identifying other suitable toxins, homologs, and derivatives are known in the art. For instance, see the RASTA-bacteria tool (Sevin E W, Barloy-Hubler F. RASTA-Bacteria: a web-based tool for identifying toxin-antitoxin loci in prokaryotes. Genome Biology 2007, 8:R155).

Exemplary examples of toxins may be found in Table 1 of the Examples.

(b) Second Promoter Operably Linked to a Nucleic Acid Encoding an Antitoxin

A *Salmonella* bacterium of the invention further comprises, in part, a second promoter operably linked to a nucleic acid encoding an antitoxin. A second promoter used herein generally allows transcription of the antitoxin nucleic acid sequence while in a permissive environment (i.e. in vitro growth), but ceases transcription of the antitoxin nucleic acid sequence while in a non-permissive environment (i.e. during growth of the bacterium in an animal or human host). The inactivation of the antitoxin promoter in vivo allows the toxin to cause the death of the bacterial cell.

For instance, the second promoter may be responsive to a physical or chemical difference between the permissive and non-permissive environment. Suitable examples of such regulatable promoters are known in the art and detailed below.

In some embodiments, the promoter may be responsive to the level of arabinose in the environment. Generally speaking, arabinose may be present during the in vitro growth of a bacterium, while typically absent from host tissue. In one embodiment, the promoter is derived from an araC-$P_{BAD}$ system. The araC-$P_{BAD}$ system is a tightly regulated expression system that has been shown to work as a strong promoter induced by the addition of low levels of arabinose. The Growth of such strains in the presence of arabinose leads to transcription of the antitoxin nucleic acid sequences, but transcription ceases in a host because there is no free arabinose. Cell death occurs as the decreasing level of antitoxin (diluted at each cell division) fails to neutralize the toxin produced.

In some embodiments, a suitable second promoter is active in a non-tumor cell, but substantially inactive in a tumor cell. "Active" and "substantially inactive" are as defined in section I(a) above. For instance, a second promoter may be modulated by a transcriptional regulator that is inactivated in a tumor cell. A non-limiting example is p53.

As used herein, "antitoxin" refers to either an amino acid polymer encoded by a nucleic acid sequence, that when translated into an amino acid, inhibits the toxic activity of a toxin, or an RNA nucleic acid sequence that inhibits the toxic activity of a toxin. The activity of an antitoxin may derive from an RNA transcript of a nucleic acid, an amino acid sequence encoded by a nucleic acid, or an RNA molecule. Non-limiting examples of antitoxins may be found in Table A. Additionally, an example of an RNA antitoxin for a Type III system is detailed in section I(a) above.

Exemplary antitoxins may be found in Table 1 of the Examples.

TABLE A

| Toxin | Antitoxin |
|---|---|
| Type I | |
| Hok | Sok |
| fst | RNAII |
| TisB | IstR |
| LdrD | RdlD |
| FlmA | FlmB |
| Ibs | Sib |
| TxpA | RatA |
| SymE | SymR |
| XCV2162 | ptaRNA1 |
| dinJ | yafQ |
| Type II | |
| CcdB | CcdA |
| ParE | ParD |
| MazF | MazE |
| yafO | yafN |
| HicB | HicA |
| Kid | Kis |
| relB | relE |
| dinJ | yafQ |
| yhaV | prlF |
| yoeB | yefM |
| chpBK | chpBI |
| hipA | hipB |

(c) Attenuation

In each of the above embodiments, a recombinant bacterium of the invention may also be attenuated. "Attenuated" refers to the state of the bacterium wherein the bacterium has been weakened from its wild-type fitness by some form of recombinant or physical manipulation. This includes altering the genotype of the bacterium to reduce its ability to cause disease. However, the bacterium's ability to colonize the host (and/or tumor) is, preferably, not substantially compromised. For instance, in one embodiment, regulated attenuation allows the recombinant bacterium to express one or more nucleic acids encoding products important for the bacterium to withstand stresses encountered in the host after immunization. This allows efficient invasion and colonization of host (and/or tumor) tissues before the recombinant bacterium is regulated to display the attenuated phenotype.

In one embodiment, a recombinant bacterium may be attenuated by regulating LPS O-antigen. In other embodiments, attenuation may be accomplished by altering (e.g., deleting) native nucleic acid sequences found in the wild type bacterium. For instance, if the bacterium is *Salmonella*, non-limiting examples of nucleic acid sequences which may be used for attenuation include: a pab nucleic acid sequence, a pur nucleic acid sequence, an aro nucleic acid sequence, asdA, a dap nucleic acid sequence, nadA, pncB, galE, pmi, fur, rpsL, ompR, htrA, hemA, cdt, cya, crp, dam, phoP, phoQ, rfc, poxA, galU, mviA, sodC, recA, ssrA, sirA, inv, hilA, rpoE, flgM, tonB, slyA, and any combination thereof. Exemplary attenuating mutations may be aroA, aroC, aroD, cdt, cya, crp, phoP, phoQ, ompR, galE, and htrA.

In certain embodiments, the above nucleic acid sequences may be placed under the control of a sugar regulated promoter wherein the sugar is present during in vitro growth of the recombinant bacterium, but substantially absent within an animal or human host. The cessation in transcription of the nucleic acid sequences listed above would then result in attenuation and the inability of the recombinant bacterium to induce disease symptoms.

The bacterium may also be modified to create a balanced-lethal host-vector system, although other types of systems may also be used (e.g., creating complementation heterozygotes). For the balanced-lethal host-vector system, the bacterium may be modified by manipulating its ability to synthesize various essential constituents needed for synthesis of the rigid peptidoglycan layer of its cell wall. In one example, the constituent is diaminopimelic acid (DAP). Various enzymes are involved in the eventual synthesis of DAP. In one example, the bacterium is modified by using a ΔasdA mutation to eliminate the bacterium's ability to produce β-aspartate semialdehyde dehydrogenase, an enzyme essential for the synthesis of DAP. One of skill in the art can also use the teachings of U.S. Pat. No. 6,872,547 for other types of mutations of nucleic acid sequences that result in the abolition of the synthesis of DAP. These nucleic acid sequences may include, but are not limited to, dapA, dapB, dapC, dapD, dapE, dapF, and asdA. Other modifications that may be employed include modifications to a bacterium's ability to synthesize D-alanine or to synthesize D-glutamic acid (e.g., Δmurl mutations), which are both unique constituents of the peptidoglycan layer of the bacterial cell wall Yet another balanced-lethal host-vector system comprises modifying the bacterium such that the synthesis of an essential constituent of the rigid layer of the bacterial cell wall is dependent on a nutrient (e.g., arabinose) that can be supplied during the growth of the microorganism. For example, a bacterium may comprise the $\Delta P_{murA}$::TT araC $P_{BAD}$ murA deletion-insertion mutation. This type of mutation makes synthesis of muramic acid (another unique essential constituent of the peptidoglycan layer of the bacterial cell wall) dependent on the presence of arabinose that can be supplied during growth of the bacterium in vitro.

Other means of attenuation are known in the art.

i. Regulated Attenuation

The present invention also encompasses a recombinant bacterium capable of regulated attenuation. Generally speaking, a bacterium capable of regulated attenuation comprises a chromosomally integrated regulatable promoter. The promoter replaces the native promoter of, and is operably linked to, at least one nucleic acid sequence encoding an attenuation protein, such that the absence of the function of the protein renders the bacterium attenuated. In some embodiments, the promoter is modified to optimize the regulated attenuation.

In each of the above embodiments described herein, more than one method of attenuation may be used. For instance, a recombinant bacterium of the invention may comprise a regulatable promoter chromosomally integrated so as to replace the native promoter of, and be operably linked to, at least one nucleic acid sequence encoding an attenuation protein, such that the absence of the function of the protein renders the bacterium attenuated, and the bacterium may comprise another method of attenuation detailed in section (c) above.

A. Attenuation Protein

Herein, "attenuation protein" is meant to be used in its broadest sense to encompass any protein the absence of which attenuates a bacterium. For instance, in some embodiments, an attenuation protein may be a protein that helps protect a bacterium from stresses encountered in the gastrointestinal tract or respiratory tract. Non-limiting examples may be the RpoS, PhoPQ, OmpR, Fur, and Crp proteins. In other embodiments, the protein may be necessary to synthesize a component of the cell wall of the bacterium, or may itself be a necessary component of the cell wall such as the protein encoded by murA.

The native promoter of at least one, two, three, four, five, or more than five attenuation proteins may be replaced by a regulatable promoter as described herein. In one embodiment, the promoter of one of the proteins selected from the group comprising RpoS, PhoPQ, OmpR, Fur, and Crp may be replaced. In another embodiment, the promoter of two, three, four or five of the proteins selected from the group comprising RpoS, PhoPQ, OmpR, Fur, and Crp may be replaced.

If the promoter of more than one attenuation protein is replaced, each promoter may be replaced with a regulatable promoter, such that the expression of each attenuation protein encoding sequence is regulated by the same compound or condition. Alternatively, each promoter may be replaced with a different regulatable promoter, such that the expression of each attenuation protein encoding sequence is regulated by a different compound or condition such as by the sugars arabinose, maltose, rhamnose or xylose.

B. Regulatable Promoter

The native promoter of a nucleic acid sequence encoding an attenuation protein is replaced with a regulatable promoter operably linked to the nucleic acid sequence encoding an attenuation protein. The term "operably linked" is defined above.

The regulatable promoter used herein generally allows transcription of the nucleic acid sequence encoding the attenuation protein while in a permissive environment (i.e. in vitro growth), but cease transcription of the nucleic acid sequence encoding an attenuation protein while in a non-permissive environment (i.e. during growth of the bacterium in an animal or human host). For instance, the promoter may be responsive to a physical or chemical difference between the permissive and non-permissive environment. Suitable examples of such regulatable promoters are known in the art.

In some embodiments, the promoter may be responsive to the level of arabinose in the environment. In other embodiments, the promoter may be responsive to the level of maltose, rhamnose, or xylose in the environment. The promoters detailed herein are known in the art, and methods of operably linking them to a nucleic acid sequence encoding an attenuation protein are known in the art.

In certain embodiments, a recombinant bacterium of the invention may comprise any of the following: $\Delta P_{fur}$::TT araC $P_{BAD}$ fur, $\Delta P_{crp}$::TT araC $P_{BAD}$ crp, $\Delta P_{phoPQ}$::TT araC $P_{BAD}$ phoPQ, or a combination thereof. Growth of such strains in the presence of arabinose leads to transcription of the fur, phoPQ, and/or crp nucleic acid sequences, but nucleic acid sequence expression ceases in a host because there is no free arabinose. Attenuation develops as the products of the fur, phoPQ, and/or the crp nucleic acid sequences are diluted at each cell division. Strains with the $\Delta P_{fur}$ and/or the $\Delta P_{phoPQ}$ mutations are attenuated at oral doses of $10^9$ CFU, even in three-week old mice at weaning. Generally speaking, the concentration of arabinose necessary to induce expression is typically less than about 2%. In some embodiments, the concentration is less than about 1.5%, 1%, 0.5%, 0.2%, 0.1%, or 0.05%. In certain embodiments, the concentration may be about 0.04%, 0.03%, 0.02%, or 0.01%. In an exemplary embodiment, the concentration is about 0.05%. Higher concentrations of arabinose or other sugars may lead to acid production during growth that may inhibit desirable cell densities. The inclusion of mutations such as ΔaraBAD or mutations that block the uptake and/or breakdown of maltose, rhamnose, or xylose, however, may prevent such acid production and enable use of higher sugar concentrations with no ill effects.

When the regulatable promoter is responsive to arabinose, the onset of attenuation may be delayed by including additional mutations, such as ΔaraBAD23, which prevents use of arabinose retained in the cell cytoplasm at the time of oral immunization, and/or ΔaraE25 that enhances retention of arabinose. Thus, inclusion of these mutations may be beneficial in at least two ways: first, enabling higher culture densities, and second enabling a further delay in the display of the attenuated phenotype that may result in higher densities in effector lymphoid tissues to further enhance immunogenicity.

C. Modifications

Attenuation of the recombinant bacterium may be optimized by modifying the nucleic acid sequence encoding an attenuation protein and/or promoter. Methods of modifying a promoter and/or a nucleic acid sequence encoding an attenuation protein are the same as those detailed above with respect to repressors in section (d)i(D).

In some embodiments, more than one modification may be performed to optimize the attenuation of the bacterium. For instance, at least one, two, three, four, five, six, seven, eight or nine modifications may be performed to optimize the attenuation of the bacterium. In various exemplary embodiments of the invention, the SD sequences and/or the start codons for the fur and/or the phoPQ virulence nucleic acid sequences may be altered so that the production levels of these nucleic acid products are optimal for regulated attenuation.

(d) Regulated Expression of at Least One Nucleic Acid Encoding an Antigen

The present invention also encompasses a recombinant bacterium capable of regulated expression of at least one nucleic acid sequence encoding an antigen. For instance, the bacterium may comprise a chromosomally integrated nucleic acid sequence encoding a repressor and a vector. Each is discussed in more detail below.

i. Chromosomally Integrated Nucleic Acid Sequence Encoding a Repressor

A recombinant bacterium of the invention that is capable of the regulated expression of at least one nucleic acid sequence encoding an antigen comprises, in part, at least one chromosomally integrated nucleic acid sequence encoding a repressor. Typically, the nucleic acid sequence encoding a repressor is operably linked to a regulatable promoter. The nucleic acid sequence encoding a repressor and/or the promoter may be modified from the wild-type nucleic acid sequence so as to optimize the expression level of the nucleic acid sequence encoding the repressor.

Methods of chromosomally integrating a nucleic acid sequence encoding a repressor operably-linked to a regulatable promoter are known in the art and detailed in the examples. Generally speaking, the nucleic acid sequence encoding a repressor should not be integrated into a locus that disrupts colonization of the host by the recombinant bacterium, or attenuates the bacterium. In one embodiment, the nucleic acid sequence encoding a repressor may be integrated into the relA nucleic acid sequence. In another embodiment, the nucleic acid sequence encoding a repressor may be integrated into the endA, ilvG or cysG nucleic acid sequences. Other suitable insertion sites can be readily identified by those with skill in the art.

In some embodiments, at least one nucleic acid sequence encoding a repressor is chromosomally integrated. In other embodiments, at least two, or at least three nucleic acid sequences encoding repressors may be chromosomally integrated into the recombinant bacterium. If there is more than one nucleic acid sequence encoding a repressor, each nucleic acid sequence encoding a repressor may be operably linked to a regulatable promoter, such that each promoter is regulated by the same compound or condition. Alternatively, each nucleic acid sequence encoding a repressor may be operably linked to a regulatable promoter, each of which is regulated by a different compound or condition.

A. Repressor

As used herein, "repressor" refers to a biomolecule that represses transcription from one or more promoters. Generally speaking, a suitable repressor of the invention is synthesized in high enough quantities during the in vitro growth of the bacterial strain to repress the transcription of the nucleic acid encoding an antigen of interest on the vector, as detailed below, and not impede the in vitro growth of the strain. Additionally, a suitable repressor will generally be substantially stable, i.e. not subject to proteolytic breakdown. Furthermore, a suitable repressor will be diluted by about half at every cell division after expression of the repressor ceases, such as in a non-permissive environment (e.g. an animal or human host).

In some embodiments, the repressor is not derived from the same species of bacteria as the recombinant bacterium. For instance, the repressor may be derived from *E. coli* if the recombinant bacterium is from the genus *Salmonella*. Alternatively, the repressor may be from a bacteriophage.

Suitable repressors are known in the art, and may include, for instance, LacI of *E. coli*, C2 encoded by bacteriophage P22, or C1 encoded by bacteriophage λ. Other suitable repressors may be repressors known to regulate the expression of a regulatable nucleic acid sequence, such as nucleic acid sequences involved in the uptake and utilization of sugars. In one embodiment, the repressor is LacI. In another embodiment, the repressor is C2. In yet another embodiment, the repressor is C1.

B. Regulatable Promoter

The chromosomally integrated nucleic acid sequence encoding a repressor is operably linked to a regulatable promoter. The regulated promoter used herein generally allows transcription of the nucleic acid sequence encoding a repressor while in a permissive environment (i.e. in vitro growth), but ceases transcription of the nucleic acid sequence encoding a repressor while in a non-permissive environment (i.e. during growth of the bacterium in an animal or human host), as detailed above. For instance, the promoter may be sensitive to a physical or chemical difference between the permissive and non-permissive environment. Suitable examples of such regulatable promoters are known in the art.

In some embodiments, the promoter may be responsive to the level of arabinose in the environment. Generally speaking, arabinose may be present during the in vitro growth of a bacterium, while typically absent from host tissue. In one embodiment, the promoter is derived from an araC-$P_{BAD}$ system. The araC-$P_{BAD}$ system is a tightly regulated expression system that has been shown to work as a strong promoter induced by the addition of low levels of arabinose. The araC-araBAD promoter is a bidirectional promoter controlling expression of the araBAD nucleic acid sequences in one direction, and the araC nucleic acid sequence in the other direction. For convenience, the portion of the araC-araBAD promoter that mediates expression of the araBAD nucleic acid sequences, and which is controlled by the araC nucleic acid sequence product, is referred to herein as $P_{BAD}$. For use as described herein, a cassette with the araC nucleic acid sequence and the araC-araBAD promoter may be used. This cassette is referred to herein as araC-$P_{BAD}$. The AraC protein is both a positive and negative regulator of $P_{BAD}$. In the presence of arabinose, the AraC protein is a positive regulatory element that allows expression from $P_{BAD}$. In the absence of arabinose, the AraC protein represses expression from $P_{BAD}$. This can lead to a 1,200-fold difference in the level of expression from $P_{BAD}$.

Other enteric bacteria contain arabinose regulatory systems homologous to the araC araBAD system from *E. coli*. For example, there is homology at the amino acid sequence level between the *E. coli* and the *S. Typhimurium* AraC proteins, and less homology at the DNA level. However, there is high specificity in the activity of the AraC proteins. For example, the *E. coli* AraC protein activates only *E. coli* $P_{BAD}$ (in the presence of arabinose) and not *S. Typhimurium* $P_{BAD}$. Thus, an arabinose regulated promoter may be used in a recombinant bacterium that possesses a similar arabinose operon, without substantial interference between the two, if the promoter and the operon are derived from two different species of bacteria.

Generally speaking, the concentration of arabinose necessary to induce expression is typically less than about 2%. In some embodiments, the concentration is less than about 1.5%, 1%, 0.5%, 0.2%, 0.1%, or 0.05%. In other embodiments, the concentration is 0.05% or below, e.g. about 0.04%, 0.03%, 0.02%, or 0.01%. In an exemplary embodiment, the concentration is about 0.05%.

In other embodiments, the promoter may be responsive to the level of maltose in the environment. Generally speaking, maltose may be present during the in vitro growth of a bacterium, while typically absent from host tissue. The malT nucleic acid encodes MalT, a positive regulator of four maltose-responsive promoters ($P_{PQ}$, $P_{EFG}$, $P_{KBM}$, and $P_S$). The combination of malT and a mal promoter creates a tightly regulated expression system that has been shown to work as a strong promoter induced by the addition of maltose. Unlike the araC-$P_{BAD}$ system, malT is expressed from a promoter ($P_T$) functionally unconnected to the other mal promoters. $P_T$ is not regulated by MalT. The malEFG-malKBM promoter is a bidirectional promoter controlling expression of the malKBM nucleic acid sequences in one direction, and the malEFG nucleic acid sequences in the other direction. For convenience, the portion of the malEFG-malKBM promoter that mediates expression of the malKBM nucleic acid sequence, and which is controlled by the malT nucleic acid sequence product, is referred to herein as $P_{KBM}$, and the portion of the malEFG-malKBM promoter that mediates expression of the malEFG nucleic acid sequence, and that is controlled by the malT nucleic acid sequence product, is referred to herein as $P_{EFG}$. Full induction of $P_{KBM}$ requires the presence of the MalT binding sites of $P_{EFG}$. For use in the vectors and systems described herein, a cassette with the malT nucleic acid sequence and one of the mal promoters may be used. This cassette is referred to herein as malT-$P_{mal}$.

In the presence of maltose, the MalT protein is a positive regulatory element that allows expression from $P_{mal}$.

In still other embodiments, the promoter may be sensitive to the level of rhamnose in the environment. Analogous to the araC-$P_{BAD}$ system described above, the rhaRS-$P_{rhaB}$ activator-promoter system is tightly regulated by rhamnose. Expression from the rhamnose promoter ($P_{rha}$) is induced to high levels by the addition of rhamnose, which is common in bacteria but rarely found in host tissues. The nucleic acid sequences rhaBAD are organized in one operon that is controlled by the $P_{rhaBAD}$ promoter. This promoter is regulated by two activators, RhaS and RhaR, and the corresponding nucleic acid sequences belong to one transcription unit that is located in the opposite direction of the rhaBAD nucleic acid sequences. If L-rhamnose is available, RhaR binds to the $P_{rhaRS}$ promoter and activates the production of RhaR and RhaS. RhaS together with L-rhamnose in turn binds to the $P_{rhaBAD}$ and the $P_{rhaT}$ promoter and activates the transcription of the structural nucleic acid sequences. Full induction of rhaBAD transcription also requires binding of the Crp-cAMP complex, which is a key regulator of catabolite repression.

Although both L-arabinose and L-rhamnose act directly as inducers for expression of regulons for their catabolism, important differences exist in regard to the regulatory mechanisms. L-Arabinose acts as an inducer with the activator AraC in the positive control of the arabinose regulon. However, the L-rhamnose regulon is subject to a regulatory cascade; it is therefore subject to even tighter control than the araC $P_{BAD}$ system. L-Rhamnose acts as an inducer with the activator RhaR for synthesis of RhaS, which in turn acts as an activator in the positive control of the rhamnose regulon. In the present invention, rhamnose may be used to interact with the RhaR protein and then the RhaS protein may activate transcription of a nucleic acid sequence operably-linked to the $P_{rha}$ promoter.

In still other embodiments, the promoter may be sensitive to the level of xylose in the environment. The xylR-$P_{xylA}$ system is another well-established inducible activator-promoter system. Xylose induces xylose-specific operons (xylE, xylFGHR, and xylAB) regulated by XylR and the cyclic AMP-Crp system. The XylR protein serves as a positive regulator by binding to two distinct regions of the xyl nucleic acid sequence promoters. As with the araC-$P_{BAD}$ system described above, the xylR-$P_{xylAB}$ and/or xylR-$P_{xylFGH}$ regulatory systems may be used in the present invention. In these embodiments, xylR $P_{xylAB}$ xylose interacting with the XylR protein activates transcription of nucleic acid sequences operably-linked to either of the two $P_{xyl}$ promoters.

The nucleic acid sequences of the promoters detailed herein are known in the art, and methods of operably-linking them to a chromosomally integrated nucleic acid sequence encoding a repressor are known in the art and detailed in the examples.

C. Modification to Optimize Expression

A nucleic acid sequence encoding a repressor and regulatable promoter detailed above, for use in the present invention, may be modified so as to optimize the expression level of the nucleic acid sequence encoding the repressor. The optimal level of expression of the nucleic acid sequence encoding the repressor may be estimated, or may be determined by experimentation (see the Examples). Such a determination should take into consideration whether the repressor acts as a monomer, dimer, trimer, tetramer, or higher multiple, and should also take into consideration the copy number of the vector encoding the antigen of interest, as detailed below. In an exemplary embodiment, the level of expression is optimized so that the repressor is synthesized while in the permissive environment (i.e. in vitro growth) at a level that substantially inhibits the expression of the nucleic acid encoding an antigen of interest, and is substantially not synthesized in a non-permissive environment, thereby allowing expression of the nucleic acid encoding an antigen of interest.

As stated above, the level of expression may be optimized by modifying the nucleic acid sequence encoding the repressor and/or promoter. As used herein, "modify" refers to an alteration of the nucleic acid sequence of the repressor and/or promoter that results in a change in the level of transcription of the nucleic acid sequence encoding the repressor, or that results in a change in the level of synthesis of the repressor. For instance, in one embodiment, modify may refer to altering the start codon of the nucleic acid sequence encoding the repressor. Generally speaking, a GTG or TTG start codon, as opposed to an ATG start codon, may decrease translation efficiency ten-fold. In another embodiment, modify may refer to altering the Shine-Dalgarno (SD) sequence of the nucleic acid sequence encoding the repressor. The SD sequence is a ribosomal binding site generally located 6-7 nucleotides upstream of the start codon. The SD consensus sequence is AGGAGG, and variations of the consensus sequence may alter translation efficiency. In yet another embodiment, modify may refer to altering the distance between the SD sequence and the start codon. In still another embodiment, modify may refer to altering the −35 sequence for RNA polymerase recognition. In a similar embodiment, modify may refer to altering the −10 sequence for RNA polymerase binding. In an additional embodiment, modify may refer to altering the number of nucleotides between the −35 and −10 sequences. In an alternative embodiment, modify may refer to optimizing the codons of the nucleic acid sequence encoding the repressor to alter the level of translation of the mRNA encoding the repressor. For instance, non-A rich codons initially after the start codon of the nucleic acid sequence encoding the repressor may not maximize translation of the mRNA encoding the repressor. Similarly, the codons of the nucleic acid sequence encoding the repressor may be altered so as to mimic the codons from highly synthesized proteins of a particular organism. In a further embodiment, modify may refer to altering the GC content of the nucleic acid sequence encoding the repressor to change the level of translation of the mRNA encoding the repressor.

In some embodiments, more than one modification or type of modification may be performed to optimize the expression level of the nucleic acid sequence encoding the repressor. For instance, at least one, two, three, four, five, six, seven, eight, or nine modifications, or types of modifications, may be performed to optimize the expression level of the nucleic acid sequence encoding the repressor.

By way of non-limiting example, when the repressor is LacI, then the nucleic acid sequence of LacI and the promoter may be altered so as to increase the level of LacI synthesis. In one embodiment, the start codon of the LacI repressor may be altered from GTG to ATG. In another embodiment, the SD sequence may be altered from AGGG to AGGA. In yet another embodiment, the codons of lacI may be optimized according to the codon usage for highly synthesized proteins of *Salmonella*. In a further embodiment, the start codon of lacI may be altered, the SD sequence may be altered, and the codons of lacI may be optimized.

Methods of modifying the nucleic acid sequence encoding the repressor and/or the regulatable promoter are known in the art and detailed in the examples.

D. Transcription Termination Sequence

In some embodiments, the chromosomally integrated nucleic acid sequence encoding the repressor further comprises a transcription termination sequence. A transcription termination sequence may be included to prevent inappropriate expression of nucleic acid sequences adjacent to the chromosomally integrated nucleic acid sequence encoding the repressor and regulatable promoter.

ii. Vector

A recombinant bacterium of the invention that is capable of the regulated expression of at least one nucleic acid sequence encoding an antigen comprises, in part, a vector. The vector comprises a nucleic acid sequence encoding at least one antigen of interest operably linked to a promoter. The promoter is regulated by the chromosomally encoded repressor, such that the expression of the nucleic acid sequence encoding an antigen is repressed during in vitro growth of the bacterium, but the bacterium is capable of high level synthesis of the antigen in an animal or human host.

As used herein, "vector" refers to an autonomously replicating nucleic acid unit. The present invention can be practiced with any known type of vector, including viral, cosmid, phasmid, and plasmid vectors. The most preferred type of vector is a plasmid vector.

As is well known in the art, plasmids and other vectors may possess a wide array of promoters, multiple cloning sequences, transcription terminators, etc., and vectors may be selected so as to control the level of expression of the nucleic acid sequence encoding an antigen by controlling the relative copy number of the vector. In some instances in which the vector might encode a surface localized adhesin as the antigen, or an antigen capable of stimulating T-cell immunity, it may be preferable to use a vector with a low copy number such as at least two, three, four, five, six, seven, eight, nine, or ten copies per bacterial cell. A non-limiting example of a low copy number vector may be a vector comprising the pSC101 ori.

In other cases, an intermediate copy number vector might be optimal for inducing desired immune responses. For instance, an intermediate copy number vector may have at least 10, 11, 12, 13, 14, 15, 16, 17, 18, 19, 20, 21, 22, 23, 24, 25, 26, 27, 28, 29, or 30 copies per bacterial cell. A non-limiting example of an intermediate copy number vector may be a vector comprising the p15A ori.

In still other cases, a high copy number vector might be optimal for the induction of maximal antibody responses. A high copy number vector may have at least 31, 35, 40, 45, 50, 55, 60, 65, 70, 75, 80, 85, 90, 95, or 100 copies per bacterial cell. In some embodiments, a high copy number vector may have at least 100, 125, 150, 175, 200, 225, 250, 275, 300, 325, 350, 375, or 400 copies per bacterial cell. Non-limiting examples of high copy number vectors may include a vector comprising the pBR ori or the pUC ori.

Additionally, vector copy number may be increased by selecting for mutations that increase plasmid copy number. These mutations may occur in the bacterial chromosome but are more likely to occur in the plasmid vector.

Preferably, vectors used herein do not comprise antibiotic resistance markers to select for maintenance of the vector.

A. Antigen

As used herein, "antigen" refers to a biomolecule capable of eliciting an immune response in a host. In some embodiments, an antigen may be a protein, or fragment of a protein, or a nucleic acid. In an exemplary embodiment, the antigen elicits a protective immune response. As used herein, "protective" means that the immune response contributes to the lessening of any symptoms associated with infection of a host with a pathogen the antigen is designed to protect against. The use of the term "protective" in this invention does not necessarily require that the host is completely protected from the effects of the pathogen.

It is not necessary that the vector comprise the complete nucleic acid sequence of the antigen. It is only necessary that the antigen sequence used be capable of eliciting an immune response. The antigen may be one that was not found in that exact form in the parent organism. For example, a sequence coding for an antigen comprising 100 amino acid residues may be transferred in part into a recombinant bacterium so that a peptide comprising only 75, 65, 55, 45, 35, 25, 15, or even 10, amino acid residues is produced by the recombinant bacterium. Alternatively, if the amino acid sequence of a particular antigen or fragment thereof is known, it may be possible to chemically synthesize the nucleic acid fragment or analog thereof by means of automated nucleic acid sequence synthesizers, PCR, or the like and introduce said nucleic acid sequence into the appropriate copy number vector.

In another alternative, a vector may comprise a long sequence of nucleic acid encoding several nucleic acid sequence products, one or all of which may be antigenic. In some embodiments, a vector of the invention may comprise a nucleic acid sequence encoding at least one antigen, at least two antigens, at least three antigens, or more than three antigens. These antigens may be encoded by two or more open reading frames operably linked to be expressed coordinately as an operon, wherein each antigen is synthesized independently. Alternatively, the two or more antigens may be encoded by a single open reading frame such that the antigens are synthesized as a fusion protein.

In certain embodiments, an antigen of the invention may comprise a B cell epitope or a T cell epitope. Alternatively, an antigen to which an immune response is desired may be expressed as a fusion to a carrier protein that contains a strong promiscuous T cell epitope and/or serves as an adjuvant and/or facilitates presentation of the antigen to enhance, in all cases, the immune response to the antigen or its component part. This can be accomplished by methods known in the art. Fusion to tetanus toxin fragment C, CT-B, LT-B and hepatitis virus B core are particularly useful for these purposes, although other epitope presentation systems are well known in the art.

In further embodiments, a nucleic acid sequence encoding an antigen of the invention may comprise a secretion signal. In other embodiments, an antigen of the invention may be toxic to the recombinant bacterium.

B. Promoter Regulated by Repressor

The vector comprises a nucleic acid sequence encoding at least one antigen operably-linked to a promoter regulated by the repressor, encoded by a chromosomally integrated nucleic acid sequence. One of skill in the art would recognize, therefore, that the selection of a repressor dictates, in part, the selection of the promoter operably-linked to a nucleic acid sequence encoding an antigen of interest. For instance, if the repressor is LacI, then the promoter may be selected from the group consisting of LacI responsive promoters, such as $P_{trc}$, $P_{lac}$, $P_{T7lac}$ and $P_{tac}$. If the repressor is C2, then the promoter may be selected from the group consisting of C2 responsive promoters, such as P22 promoters $P_L$ and $P_R$. If the repressor is C1, then the promoter may be selected from the group consisting of C1 responsive promoters, such as λ, promoters $P_L$ and $P_R$.

In each embodiment herein, the promoter regulates expression of a nucleic acid sequence encoding the antigen, such that expression of the nucleic acid sequence encoding an antigen is repressed when the repressor is synthesized (i.e.

during in vitro growth of the bacterium), but expression of the nucleic acid sequence encoding an antigen is high when the repressor is not synthesized (i.e. in an animal or human host). Generally speaking, the concentration of the repressor will decrease with every cell division after expression of the nucleic acid sequence encoding the repressor ceases. In some embodiments, the concentration of the repressor decreases enough to allow high level expression of the nucleic acid sequence encoding an antigen after about 2, 3, 4, 5, 6, 7, 8, 9, 10, 11, or 12 divisions of the bacterium. In an exemplary embodiment, the concentration of the repressor decreases enough to allow high level expression of the nucleic acid sequence encoding an antigen after about 5 divisions of the bacterium in an animal or human host.

In certain embodiments, the promoter may comprise other regulatory elements. For instance, the promoter may comprise lacO if the repressor is LacI. This is the case with the lipoprotein promoter $P_{lpp}$ that is regulated by LacI since it possesses the LacI binding domain lacO.

In one embodiment, the repressor is a LacI repressor and the promoter is $P_{trc}$.

C. Expression of the Nucleic Acid Sequence Encoding an Antigen

As detailed above, generally speaking the expression of the nucleic acid sequence encoding the antigen should be repressed when the repressor is synthesized. For instance, if the repressor is synthesized during in vitro growth of the bacterium, expression of the nucleic acid sequence encoding the antigen should be repressed. Expression may be "repressed" or "partially repressed" when it is about 50%, 45%, 40%, 35%, 30%, 25%, 20%, 15%, 10%, 5%, 1%, or even less than 1% of the expression under non-repressed conditions. Thus although the level of expression under conditions of "complete repression" might be exceeding low, it is likely to be detectable using very sensitive methods since repression can never by absolute.

Conversely, the expression of the nucleic acid sequence encoding the antigen should be high when the expression of the nucleic acid sequence encoding the repressor is repressed. For instance, if the nucleic acid sequence encoding the repressor is not expressed during growth of the recombinant bacterium in the host, the expression of the nucleic acid sequence encoding the antigen should be high. As used herein, "high level" expression refers to expression that is strong enough to elicit an immune response to the antigen. Consequently, the copy number correlating with high level expression can and will vary depending on the antigen and the type of immune response desired. Methods of determining whether an antigen elicits an immune response such as by measuring antibody levels or antigen-dependant T cell populations or antigen-dependant cytokine levels are known in the art, and methods of measuring levels of expression of antigen encoding sequences by measuring levels of mRNA transcribed or by quantitating the level of antigen synthesis are also known in the art.

iii. crp Cassette

In some embodiments, a recombinant bacterium of the invention may also comprise a $\Delta P_{crp}$::TT araC $P_{BAD}$ crp deletion-insertion mutation. Since the araC $P_{BAD}$ cassette is dependent both on the presence of arabinose and the binding of the catabolite repressor protein Crp, a $\Delta P_{crp}$::TT araC $P_{BAD}$ crp deletion-insertion mutation may be included as an additional means to reduce expression of any nucleic acid sequence under the control of the $P_{BAD}$ promoter. This means that when the bacterium is grown in a non-permissive environment (i.e. no arabinose) both the repressor itself and the Crp protein cease to be synthesized, consequently eliminating both regulating signals for the araC $P_{BAD}$ regulated nucleic acid sequence. This double shut off of araC $P_{BAD}$ may constitute an additional safety feature ensuring the genetic stability of the desired phenotypes.

Generally speaking, the activity of the Crp protein requires interaction with cAMP, but the addition of glucose, which may inhibit synthesis of cAMP, decreases the ability of the Crp protein to regulate transcription from the araC $P_{BAD}$ promoter. Consequently, to avoid the effect of glucose on cAMP, glucose may be substantially excluded from the growth media, or variants of crp may be isolated that synthesize a Crp protein that is not dependent on cAMP to regulate transcription from $P_{BAD}$. This strategy may also be used in other systems responsive to Crp, such as the systems responsive to rhamnose and xylose described above.

(e) Regulated Cell Death

In some embodiments, a recombinant bacterium may comprise a method of regulated delayed lysis in vivo that prevents bacterial persistence in vivo and survival if excreted. Non-limiting examples of suitable mutations may include: Δ(gmd-fcl)-26 that precludes synthesis of colanic acid that can protect cells undergoing cell wall-less death from lysing completely (f) Enhanced Stimulation of Host Anti-Tumor Immune Response The human immune system naturally grows stronger while fighting bacteria, including *Salmonella*. It is widely believed that one of the main triggers of host inflammation is the recognition of microbial products by receptors of the innate immune system. Consequently, in some embodiments, a recombinant bacterium of the invention may be engineered to express one or more proteins to stimulate host immune responses.

In one embodiment, such a protein may be guanidyl nucleotide exchange factor SopE2 and/or an inositol polyphosphatase SopB, that activate Rho-family GTPases in a functionally redundant manner to mediate the innate immune responses. In some embodiments, the native promoter of these proteins may be replaced with $P_{trc}$ to enable the regulated delayed synthesis of SopE2 and/or SopB. In certain embodiments, the start codon of the sopE2 and/or sopB genes may be modified to alter its expression level. For instance, the start codon may be changed from GTG to ATG. In addition, the second and third codons can be made more A rich to further increase translation efficiency.

II. Compositions and Administration

A recombinant bacterium of the invention may be administered to a host as a vaccine or pharmaceutical composition. As used herein, a vaccine composition is a composition designed to elicit an immune response to the recombinant bacterium, including any antigens that may be expressed by the bacterium. In an exemplary embodiment, the immune response is protective, as described above. Immune responses to antigens are well studied and widely reported. A survey of immunology is given by Paul, W E, Stites D et. al. and Ogra P L. et. al. Mucosal immunity is also described by Ogra P L et. al.

Vaccine compositions of the present invention may be administered to any host capable of mounting an immune response. Pharmaceutical compositions of the present invention may be administered to any host susceptible to tumors and the recombinant bacterium. In both instances, such hosts may include all vertebrates, for example, mammals, including domestic animals, agricultural animals, laboratory animals, and humans. Preferably, the host is a warm-blooded animal. The vaccine can be administered as a prophylactic or for treatment purposes.

In exemplary embodiments, the recombinant bacterium is alive when administered to a host in a composition of the invention. Suitable composition formulations and methods of administration are detailed below.

(a) Vaccine Composition

A vaccine composition comprising a recombinant bacterium of the invention may optionally comprise one or more possible additives, such as carriers, preservatives, stabilizers, adjuvants, and other substances.

In one embodiment, the vaccine comprises an adjuvant. Adjuvants, such as aluminum hydroxide or aluminum phosphate, are optionally added to increase the ability of the vaccine to trigger, enhance, or prolong an immune response. In exemplary embodiments, the use of a live attenuated recombinant bacterium may act as a natural adjuvant, obviating the need for any additional adjuvants. The vaccine compositions may further comprise additional components known in the art to improve the immune response to a vaccine, such as T cell co-stimulatory molecules or antibodies, such as anti-CTLA4. Additional materials, such as cytokines, chemokines, and bacterial nucleic acid sequences naturally found in bacteria, like CpG, are also potential vaccine adjuvants.

In another embodiment, the vaccine may comprise a pharmaceutical carrier (or excipient). Such a carrier may be any solvent or solid material for encapsulation that is non-toxic to the inoculated host and compatible with the recombinant bacterium. A carrier may give form or consistency, or act as a diluent. Suitable pharmaceutical carriers may include liquid carriers, such as normal saline and other non-toxic salts at or near physiological concentrations, and solid carriers not used for humans, such as talc or sucrose, or animal feed. Carriers may also include stabilizing agents, wetting and emulsifying agents, salts for varying osmolarity, encapsulating agents, buffers, and skin penetration enhancers. Carriers and excipients as well as formulations for parenteral and nonparenteral drug delivery are set forth in Remington's Pharmaceutical Sciences 19th Ed. Mack Publishing (1995). When used for administering via the bronchial tubes, the vaccine is preferably presented in the form of an aerosol.

Care should be taken when using additives so that the live recombinant bacterium is not killed, or have its ability to effectively colonize lymphoid tissues such as the GALT, NALT and BALT compromised by the use of additives. Stabilizers, such as lactose or monosodium glutamate (MSG), may be added to stabilize the vaccine formulation against a variety of conditions, such as temperature variations or a freeze-drying process.

The dosages of a vaccine composition of the invention can and will vary depending on the recombinant bacterium, the regulated antigen, and the intended host, as will be appreciated by one of skill in the art. Generally speaking, the dosage need only be sufficient to elicit a protective immune response in a majority of hosts. Routine experimentation may readily establish the required dosage. Typical initial dosages of vaccine for oral administration could be about $1 \times 10^7$ to $1 \times 10^{10}$ CFU depending upon the age of the host to be immunized. Administering multiple dosages may also be used as needed to provide the desired level of protective immunity.

(b) Pharmaceutical Composition

A pharmaceutical composition comprising a recombinant bacterium of the invention may optionally comprise one or more possible additives, such as carriers, preservatives, stabilizers, and other substances.

In another embodiment, the composition may comprise a pharmaceutical carrier (or excipient). Such a carrier may be any solvent or solid material for encapsulation that is non-toxic to the inoculated host and compatible with the recombinant bacterium. A carrier may give form or consistency, or act as a diluent. Suitable pharmaceutical carriers may include liquid carriers, such as normal saline and other non-toxic salts at or near physiological concentrations, and solid carriers not used for humans, such as talc or sucrose, or animal feed. Carriers may also include stabilizing agents, wetting and emulsifying agents, salts for varying osmolarity, encapsulating agents, buffers, and skin penetration enhancers. Carriers and excipients as well as formulations for parenteral and nonparenteral drug delivery are set forth in Remington's Pharmaceutical Sciences 19th Ed. Mack Publishing (1995). When used for administering via the bronchial tubes, the pharmaceutical composition is preferably presented in the form of an aerosol.

Care should be taken when using additives so that the live recombinant bacterium is not killed, or have its ability to effectively colonize tumor tissues compromised by the use of additives. Stabilizers, such as lactose or monosodium glutamate (MSG), may be added to stabilize the pharmaceutical formulation against a variety of conditions, such as temperature variations or a freeze-drying process. The dosages of a pharmaceutical composition of the invention can and will vary depending on the recombinant bacterium, the regulated antigen or effector protein, and the intended host, as will be appreciated by one of skill in the art. Generally speaking, the dosage need only be sufficient to elicit an anti-tumor response in a majority of hosts. Routine experimentation may readily establish the required dosage. Typical initial dosages of a pharmaceutical composition for oral administration could be about $1 \times 10^7$ to $1 \times 10^{10}$ CFU depending upon the age of the host to be immunized. Administering multiple dosages may also be used as needed to provide the desired level of anti-tumor activity.

(c) Methods of Administration

In order to stimulate a preferred response of the GALT, NALT or BALT cells, administration of the vaccine composition directly into the gut, nasopharynx, or bronchus is preferred, such as by oral administration, intranasal administration, gastric intubation or in the form of aerosols, although other methods of administering the recombinant bacterium, such as intravenous, intramuscular, subcutaneous injection or intramammary, intrapenial, intrarectal, vaginal administration, or other parenteral routes, are possible. A pharmaceutical composition may be administered orally intravenously, intramuscularly, or by subcutaneous injection.

In some embodiments, these compositions are formulated for administration by injection (e.g., intraperitoneally, intravenously, subcutaneously, intramuscularly, etc.). Accordingly, these compositions are preferably combined with pharmaceutically acceptable vehicles such as saline (including buffered saline), Ringer's solution, dextrose solution, and the like.

III. Kits

The invention also encompasses kits comprising any one of the compositions above in a suitable aliquot for vaccinating a host in need thereof. In one embodiment, the kit further comprises instructions for use. In other embodiments, the composition is lyophilized such that addition of a hydrating agent (e.g., buffered saline) reconstitutes the composition to generate a vaccine composition ready to administer, preferably orally.

IV. Methods of Use

A further aspect of the invention encompasses methods of using a recombinant bacterium of the invention. For instance, in one embodiment the invention provides a method for modulating a host's immune system. The method comprises administering to the host an effective amount of a composition comprising a recombinant bacterium of the invention. One of skill in the art will appreciate that an effective amount of a composition is an amount that will generate the desired immune response (e.g., mucosal, humoral or cellular). Methods of monitoring a host's immune response are well-known to physicians and other skilled practitioners. For instance, assays such as ELISA, and ELISPOT may be used. Effectiveness may be determined by monitoring the amount of the antigen of interest remaining in the host, or by measuring a decrease in disease incidence caused by a pathogen in a host. For certain pathogens, cultures or swabs taken as biological samples from a host may be used to monitor the existence or amount of pathogen in the individual.

In still another embodiment, a recombinant bacterium of the invention may be used in a method for eliciting an immune response against an antigen in an individual in need thereof. The method comprises administrating to the host an effective amount of a composition comprising a recombinant bacterium as described herein.

DEFINITIONS

As used herein, the term "promoter" includes all sequences capable of driving transcription of a nucleic acid sequence in a cell. Thus, promoters used in the constructs of the invention include cis-acting transcriptional control elements and regulatory sequences that are involved in regulating or modulating the timing and/or rate of transcription of a nucleic acid sequence. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) transcription.

The term "operably linked," as used herein, means that expression of a nucleic acid sequence is under the control of a promoter with which it is spatially connected. A promoter may be positioned 5' (upstream) of the nucleic acid sequence under its control. The distance between the promoter and a nucleic acid sequence to be expressed may be approximately the same as the distance between that promoter and the native nucleic acid sequence it controls. As is known in the art, variation in this distance may be accommodated without loss of promoter function.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

The following examples illustrate various iterations of the invention.

Example 1

Evaluation of a Strategy Based on the Killing Effect of Different Prokaryotic Toxins Under the Control of AraC pBAD Promoter as a Programmed Death System in Salmonella-Based Vaccine to Efficiently Release Protective Antigens and Confer Biological Containment An issue of concern when using a live vaccine is the likelihood that Salmonella vaccines for humans would induce disease symptoms and diarrhea. To increase the efficacy and the safety of the vaccine strains and to avoid the side effects related to a live vaccine, a biological containment system may be developed and evaluated that will allow the vaccine strain time to colonize the host lymphoid tissues, a requirement for inducing a robust immune response, but will also lead to cell death by lysis, thus preventing persistence of the vaccine strain in the host and the environment. This approach may prove to be more effective than others because immune responses, especially antibody responses, are highly enhanced when the antigen is released into the extracellular environment rather than being sequestered in the bacterial cytoplasm.

Figure 1:
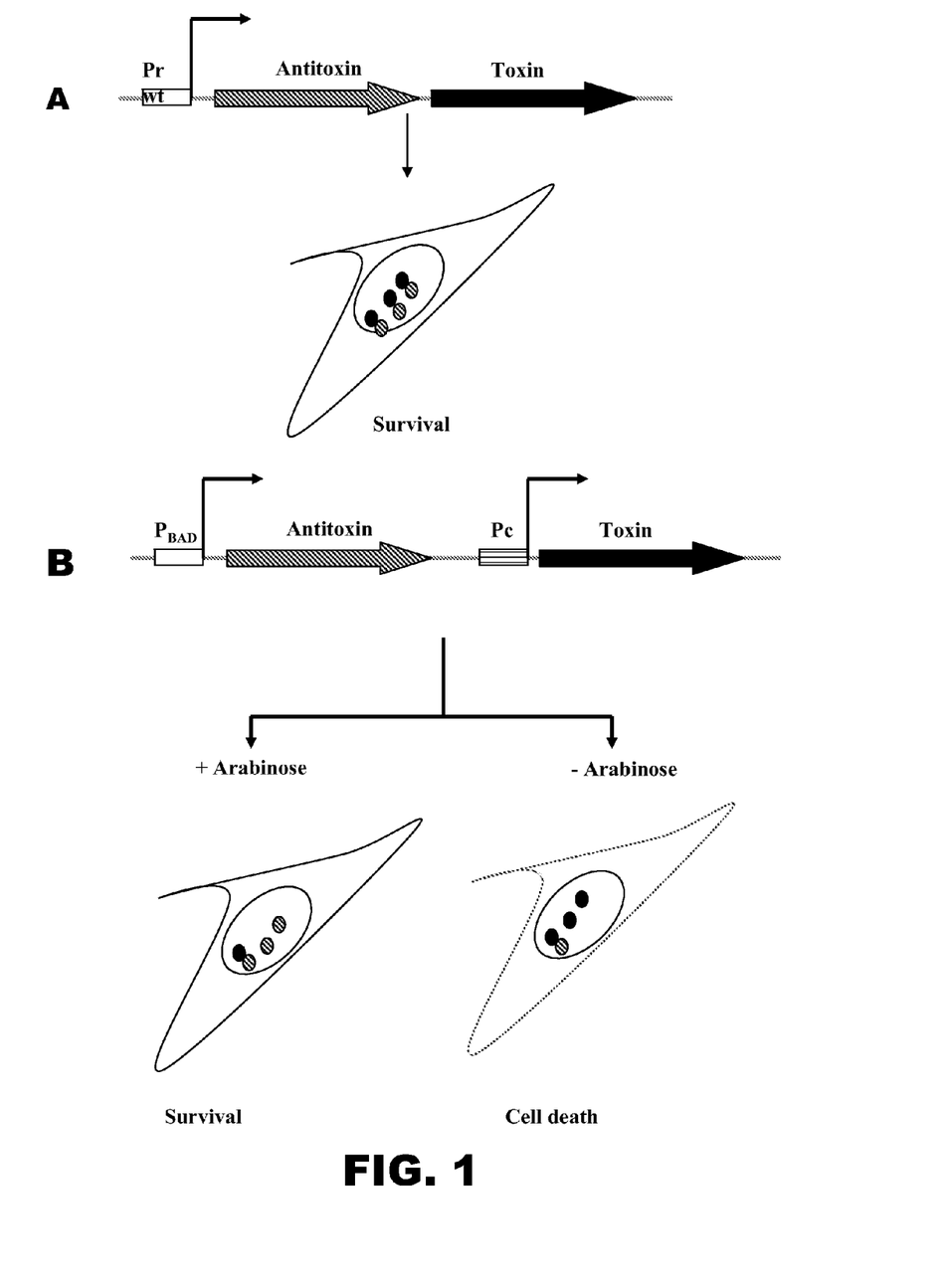
FIG. 1. Expression of toxin and its antitoxin in normal conditions. (A). Regulation expression of toxin and its antitoxin under independent transcriptional control for delayed cell death. (B). Pc a constitutive promoter, $P_{BAD}$ AraC $P_{BAD}$, arabinose dependant promoter.
Figure 2:
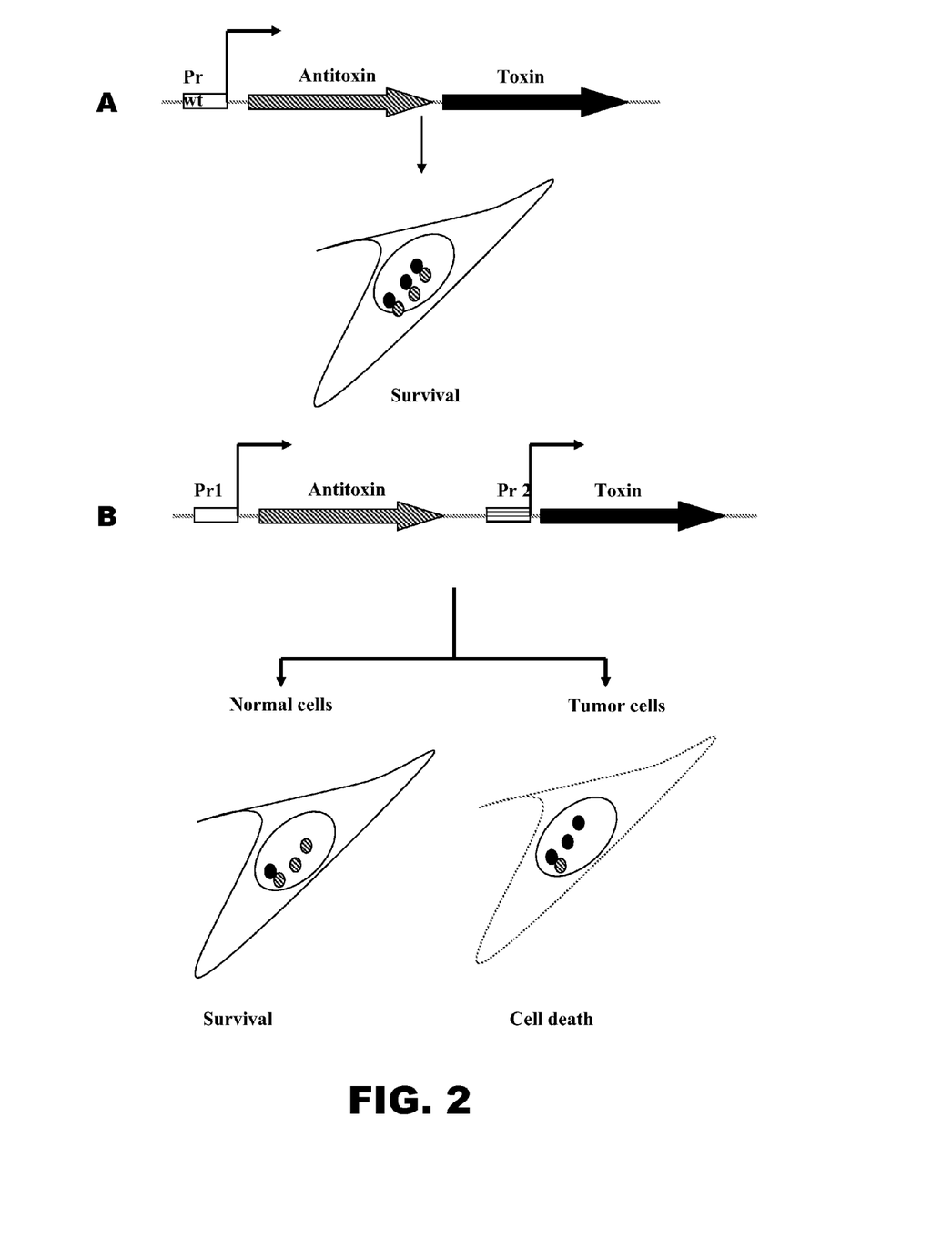
FIG. 2. Expression of toxin and its antitoxin in normal conditions (A). Regulation expression of toxin and its antitoxin under independent transcriptional control for selective killing of cancer cells (B). Pr1, promoter regulated by p53, a tumor repressor protein; Pr2, promoters induced in tumor cells.

TA systems may be considered as potential tools for biological containment. Highly selective targeting or expression of toxins may delay and maximize the bacteria cell death in host cells. To achieve this goal, independent transcriptional controls for the toxin and its antitoxin may be used rather than the native bi-cistronic structure of TA operons (FIG. 1). The gene of the toxin may be under the control of an original promoter that is constitutive in Salmonella, such as Lpp, and the gene of the antidote may be under the control of the AraC $P_{BAD}$ promoter. The AraC protein is both a positive and negative regulator of $P_{BAD}$. In the presence of arabinose, the AraC protein is a positive regulatory element that allows expression of $P_{BAD}$. In the absence of arabinose, the AraC protein represses expression from $P_{BAD}$. This can lead to a 1,200-fold difference in the level of expression from $P_{BAD}$. Under the control of the AraC $P_{BAD}$ promoter, the gene of the antidote may not be expressed in host tissues; in absence of its antidote, the toxin may cause the death of the Salmonella vaccine cells, either by lysis, apoptosis, or other means (FIG. 1).

Since different toxins and antitoxins differ functionally and structurally, their efficacy as a cell death system in vivo might be different. Therefore different groups of TA systems (Table 1) may be tested. The ability of the programmed TA system to cause the death of the cells and generate the highest immunity in mice may then be evaluated in vivo and in vitro.

TABLE 1

Different groups of TA systems according to their effects on cell death.

| Group | TA | Death process |
|---|---|---|
| 1 | mazEF | In both liquid and biofilm formation |
| 2 | relBE | Only in liquid medium |
| 3 | chpBIK yefM-yoeB | Only in liquid medium in certain conditions |
| 4 | dinJ-yafQ | Only in biofilm formation not in liquid |

Example 2

Evaluation of the Salmonella TA System Under In Vitro and In Vivo Conditions

Standard molecular and genetic procedures may be used to engineer different TA systems. The TA systems may be validated in different recombinant attenuated *Salmonella Typhimurium*. Expression of the toxin and its anti-toxin may be assessed by RT-PCR in bacteria grown in different media conditions (LB and minimal media) with and without arabinose. For analysis of toxin and its antitoxin expression during *Salmonella* infection of human epithelial cells and macrophages, selective capture of transcribed sequences (SCOTS) may be performed.

Cell death may be evaluated in vitro by growing bacteria in LB broth supplemented with 0.002% arabinose. This low concentration of arabinose may be used to prevent the accumulation of arabinose within bacterial cells to allow the detection of cell death during the short time frame used for this experiment. The growth rate of the bacteria culture at different time points and the fluorescence-based live-dead assay can be used to confirm the death of cells.

Colonization of mice with the regulated programmed death *Salmonella* vaccine strain may be tested in seven-week-old female BalB/c mice. Mice may be killed at 3, 7, 14, and 21 days post-inoculation. The Peyer's patches, spleens, and livers of the mice may be collected aseptically for bacterial analysis to evaluate colonization and persistence.

Example 3

Evaluation of Killing Effect of Different Prokaryotic Toxins Under the Control of Different Promoters on Cancer Cells The use of bacteria and their products as anti-tumor agents is an incredibly innovative approach to treating cancer. Motile facultative anaerobic bacteria, including *Salmonella*, have the potential to penetrate into tumor tissue and overcome diffusion limitations. The advantage of using *Salmonella* as a "Trojan horse" against cancers is due to the fact that this bacterium infects both phagocytic and non-phagocytic cells and replicates within privileged *Salmonella*-containing vacuoles (SCV) to induce appropriate immune response. Moreover, *Salmonella* naturally infects dendritic cells, which play a central role in triggering effective anti-tumor immunity. *Salmonella* also targets non-hypoxic regions and metastases and preferentially accumulates in tumor cells retarding their growth through competition for nutrients and by stimulating the immune system. Additionally, since oral vaccination with attenuated *S. Typhimurium* seems to be more effective in protecting against cancer than subcutaneous injection, *Salmonella*-based treatments will be less expensive, easier to use, and more accessible to low income patients.

The results of recent studies are very encouraging in pursuing the use of attenuated bacteria in cancer treatment; however more studies are needed to increase both the safety and efficacy of the treatment. Means of attenuating *Salmonella* to make it safe as a vector for treatment, or as a carrier for drugs, either render strains susceptible to various host defenses and impair its ability to invade and effectively colonize tissues or does not reduce its persistence, causing septicemic infection. To circumvent these problems, *Salmonella Typhimurium* may be genetically engineered to display both delayed attenuation and delayed lysis in order to deliver anti-tumor prokaryotic toxins under the control of promoters preferentially expressed in tumor cells with the goal of shrinking or eliminating these tumors.

While invasive *Salmonella* species naturally do not induce apoptosis in tumor cells, *Salmonella* can retard growth of tumor cells. In addition, *Salmonella* are able to express exogenous genes within tumors, allowing genetically engineered *Salmonella* to deliver toxin into tumor cells to cause their death, enhancing the efficacy of our treatment. Toxins of pathogenic bacteria have valuable practical applications because of their ability to attack eukaryotic cells. A high degree of selectivity could be achieved if the toxin is targeted to tumor cells and non-tumor cells are protected from the action of the toxin by a specific antidote.

Recently, bacterial toxins encoded with their antidote have been discovered and called toxin-antitoxin (TA) systems. They are found in both bacterial chromosomes and mobile genetic elements. These systems were first identified in bacterial plasmid maintenance where they cause the selective killing of plasmid-free daughter cells (post-segregational killing or addiction phenomena) and were later found to be present in both bacterial and archaeal chromosomes. TA system operons generally consist of two open reading frames encoding a toxin and an antitoxin gene (FIG. 2). The function of TA systems relies on a difference in stability between toxin and its antitoxin, with the toxin being more resistance to protease degradation than its antitoxin. The TAs are currently classified into two major types on the basis of the nature of the antitoxin. Type-1 TA systems, including dinJ-yafQ, hok, symER, and tisAB/istr1, consist of an RNA antitoxin and a protein toxin, in which the RNA antitoxin inhibits translation of the toxin mRNA. Type-2 TA systems, including relBE, mazEF, dinJ-yafQ, prlF-yhaV, yefM20 yoeB, chpBI-chpBK and hipAB, typically consist of two genes in an operon, transcriptionally and translationally coupled, in which, usually the upstream gene encodes a labile antitoxin protein and the downstream gene a stable toxin protein. Mechanisms of action of TAs may vary. In some instances, they may inhibit DNA gyrase or cleave RNA.

TA systems have not been considered as potential tools for targeting eukaryotic cells in the past because they were only thought to be involved in killing bacteria. However, recent studies have shown that the toxin of TA systems can trigger apoptosis in human cells, regulate cell proliferation in yeast and metazoan cells, and lead to apoptosis and decreased proliferation of cancer-derived cells. The additional fact that these actions are inhibited by their antidote has opened the door to using them in cancer therapy.

Highly selective targeting or expression of toxins to cancer cells would incur maximum damage to tumors whilst minimizing damage to normal cells and would be a safe and efficient treatment against cancer. To achieve this goal, independent transcriptional controls for the toxin and its antitoxin may be used, rather than the native bicistronic structure of TA operons (FIG. 2). The gene of the toxin may be under the control of the pflE or ansB promoter, two prokaryotic promoters known to be induced in the hypoxic conditions common to many tumors, or under the control of the eukaryotic promoter human telomerase reverse transcriptase (hTERT) that confines gene expression strictly to the telomerase-positive cancer cells. The gene of the antidote may be under the control of a promoter with a transcriptional regulator known to be inactivated in cancer cells, such as p53, to drive its expression in normal cells antagonizing the effect of the residual toxin (FIG. 2). Since different toxins and antitoxins differ functionally and structurally, their efficacy in inducing apoptosis in tumor cells might be different. Therefore different groups of TA systems (Table 1) may be tested. The ability of the engineered attenuated *Salmonella* described here to selectively deliver bacteria toxins into tumor cells in vivo and in vitro may then be evaluated. This "inside-out" approach may lead to systemic anti-tumor immunity and prevent metastasis.

Example 4

Increasing the Ability of Attenuated Bacteria to Elicit Effective Anti-Tumor Cellular Immunity and Apoptosis of Tumor Cells The success of tumor growth and metastasis in cancer patients is related to the suppression of their immune system, mainly by inhibition of T cell functions. To elicit a high level of T cells (CD4+ and CD8+) required for anticancer activity by the *Salmonella*-based treatment, *Salmonella* that includes a SPI5 sopB mutation may be used. *Salmonella* that include a sopB mutation have been proven to not only induce a high level of T cells, but also impair the ability of *Salmonella* to cause local inflammation and fluid secretion in the intestinal lumen. Additionally, since the SopB protein is known to protect *Salmonella*-infected cells from apoptosis by sustained activation of Akt, apoptosis may then no longer be inhibited in sopB mutants, which may increase the killing effect of the treatment on tumor cells.

Example 5

Evaluation of the *Salmonella* TA System Under In Vitro and In Vivo Conditions Standard molecular and genetic procedures may be used to engineer different TA systems. The TA systems may be validated in different recombinant attenuated *Salmonella Typhimurium*. Expression of the toxin and its anti-toxin may be assessed by RT-PCR in bacteria grown in different media conditions (LB and minimal media). For analysis of toxin and its antitoxin expression during *Salmonella* infection of human epithelial cells and macrophages, selective capture of transcribed sequences (SCOTS) may be performed.

Example 6

In Vitro and In Vivo Tests to Evaluate the Efficacy of Treatment in Eradicating Tumors Some studies have shown that bacteria-based treatments have the potential to treat cancer, unfortunately, they were unsuccessful in human clinical trials. The discrepancy in treatment efficacy could be due to the in vitro or in vivo tests used to evaluate the product as they may not be representative of real conditions of the human host. In this example, treatment may be evaluated in in vitro and in vivo conditions known to highly mimic the human host conditions as described below.

Cell Biology.

The efficacy of anticancer drugs is usually tested in two-dimensional (2-D) monolayers in culture plates. This is not representative of the actual nature of tumor cells. In this example, three-dimensional (3-D) cell cultures that mimic the 3-D nature of cancer cells may be used. The following tumor cell lines from ATCC may be used: breast (MCF-7 and SF-BR-3), colorectal adenocarcinoma (SW-480) and melanoma (A-375) cell lines. The various engineered *Salmonella* strains may be tested for their ability to attach, invade, and survive in cells, and to induce pyroptosis/apoptosis with methods previously described. Gene transcription of toxin and its antidote may be evaluated by RT-PCR in both normal and cancer cell lines.

Mouse Tumor Model and Bacterial Infection.

Spontaneous tumor models are considered more suitable for studying either prophylactic or therapeutic vaccination because of their similarity to human tumors in their invasiveness, metastasis and expression of common tumor-associated antigens. Moreover, mouse models now exist for different cancers. Mice may be used for growth models and infection studies as described before. Mice may be infected either orally or intravenously. Internal organs and tumor tissues may be harvested aseptically. All animals may be housed in BSL2 containment with filter bonnet covered cages. The induction of immune responses in animals (humoral and cell-mediated) may be monitored.

---

---

What is claimed is:

1. A recombinant *Salmonella* bacterium, the bacterium comprising a first promoter operably linked to a nucleic acid encoding a toxin and a second regulatable promoter operably linked to a nucleic acid encoding an antitoxin, such that transcription of the nucleic acid encoding the antitoxin occurs in a permissive in vitro environment, but ceases in a non-permissive in vivo environment.

2. The recombinant *Salmonella* bacterium of claim 1, wherein the first promoter is selected from the group consisting of the native promoter of the toxin and a constitutive promoter.

3. The recombinant *Salmonella* bacterium of claim 1, wherein the nucleic acid encoding a toxin is selected from the group consisting of fst, XCV2162, yafO, relB, dinJ, yhaV, yoeB, chpBK, and hipA or a nucleic acid that encodes a protein selected from the group consisting of Hok, TisB, LdrD, FlmA, lbs, TxpA, SymE, CcdB, ParE, MazF, HicB, Kid and ToxN.

4. The recombinant *Salmonella* bacterium of claim 1, wherein the nucleic acid encoding a toxin is selected from the group consisting of fst, yafO, relB, dinJ, yhaV, yoeB, chpBK, and hipA or a nucleic acid that encodes a protein selected from the group consisting of Hok, TisB, LdrD, FlmA, lbs, TxpA, SymE, XCV2162, CcdB, ParE, MazF, HicB, Kid and ToxN, and the first promoter operably linked to the nucleic acid encoding the toxin is the native promoter of the toxin.

5. The recombinant *Salmonella* bacterium of claim 1, wherein the first promoter is selected from the group consisting of a pflE promoter, an ansB promoter, and a human telomerase reverse transcriptase (hTERT) promoter.

6. The recombinant *Salmonella* bacterium of claim 1, wherein the second promoter is an araC-$P_{BAD}$ promoter system.

7. The recombinant *Salmonella* bacterium of claim 1, wherein the nucleic acid encoding an antitoxin is selected from the group consisting of Sok, RNAII, IstR, RdlD, FImB, Sib, RatA, SymR, PtaRNA1, yafN, relE, yafQ, prlF, yefM, chpBI, hipB and 5.5 direct repeats of SEQ ID NO:1 or a nucleic acid that encodes a protein selected from the group consisting of CcdA, ParD, MazE, HicA and Kis.

8. The recombinant *Salmonella* bacterium of claim 1, wherein the bacterium is attenuated.

9. The recombinant *Salmonella* bacterium of claim 1, wherein the bacterium further comprises a sopB mutation.

10. A method for expressing toxin in tumor cells to cause their death in a subject, the method comprising administering to the subject a recombinant *Salmonella* bacterium, the bacterium comprising a first promoter operably linked to a nucleic acid encoding a toxin and a second regulatable promoter operably linked to a nucleic acid encoding an antitoxin, such that transcription of the nucleic acid encoding the antitoxin occurs in a permissive in vitro environment, but ceases in a non-permissive in vivo environment.

11. The method of claim 10, wherein the bacterium is capable of regulated expression of at least one nucleic acid sequence encoding an antigen, wherein the antigen induces an immune response against the bacterium.

12. The method of claim 11, wherein the bacterium induces a protective immune response.

13. A vaccine composition, the vaccine composition comprising the recombinant *Salmonella* bacterium of claim 1.

14. The vaccine composition of claim 13, wherein the bacterium is capable of regulated expression of at least one nucleic acid sequence encoding an antigen, wherein the antigen induces an immune response against the bacterium.

15. The vaccine composition of claim 14, wherein the bacterium induces a protective immune response.

* * * * *